United States Patent
Hsu et al.

[11] Patent Number: 6,119,043
[45] Date of Patent: *Sep. 12, 2000

[54] ATRIAL AND VENTRICULAR CARDIAC LEAD HAVING A MECHANICAL BIAS

[75] Inventors: William Hsu, Circle Pines; Jay A. Warren, North Oaks; Gerrard M. Carlson, Champlin, all of Minn.

[73] Assignee: Cardiac Pacemakers, Inc., St. Paul, Minn.

[*] Notice: This patent is subject to a terminal disclaimer.

[21] Appl. No.: 09/129,348

[22] Filed: Aug. 5, 1998

Related U.S. Application Data

[62] Division of application No. 08/996,355, Dec. 22, 1997, Pat. No. 5,885,221, which is a continuation of application No. 08/579,872, Dec. 28, 1995, Pat. No. 5,776,072.

[51] Int. Cl.$^7$ ...................................................... A61N 1/00
[52] U.S. Cl. ............................................................ 607/123
[58] Field of Search .................................... 607/122, 123, 607/125, 4

[56] References Cited

U.S. PATENT DOCUMENTS

| | | | |
|---|---|---|---|
| Re. 30,366 | 8/1980 | Rasor et al. | 128/419 |
| 3,835,845 | 9/1974 | Maher | 128/64 |
| 4,013,081 | 3/1977 | Kolenik | 128/419 |
| 4,136,703 | 1/1979 | Wittkampf . | |
| 4,154,247 | 5/1979 | O'Neill | 128/419 P |
| 4,235,246 | 11/1980 | Weiss | 128/758 |
| 4,299,239 | 11/1981 | Weiss et al. | 128/785 |
| 4,311,153 | 1/1982 | Smits | 128/785 |
| 4,326,534 | 4/1982 | Axelgaard et al. | 128/421 |
| 4,497,326 | 2/1985 | Curry | 128/785 |
| 4,553,548 | 11/1985 | Varrichio et al. | 128/421 |
| 4,603,705 | 8/1986 | Speicher et al. . | |
| 4,627,439 | 12/1986 | Harris | 607/125 |
| 4,667,686 | 5/1987 | Peers-Travarton | 128/785 |
| 4,721,115 | 1/1988 | Owens | 128/713 |
| 4,799,486 | 1/1989 | DuFault . | |
| 4,799,493 | 1/1989 | DuFault . | |
| 4,819,662 | 4/1989 | Heil et al. | 128/786 |
| 4,967,766 | 11/1990 | Bradshaw | 128/785 |
| 4,969,463 | 11/1990 | Dahl et al. | 128/419 |
| 5,044,375 | 9/1991 | Bach, Jr. et al. | 128/786 |
| 5,074,313 | 12/1991 | Dahl et al. | 128/784 |
| 5,107,834 | 4/1992 | Ideker et al. | 128/419 |
| 5,203,348 | 4/1993 | Dahl et al. | 128/784 |
| 5,217,028 | 6/1993 | Dutcher et al. | 128/785 |
| 5,230,337 | 7/1993 | Dahl et al. | 607/5 |
| 5,269,319 | 12/1993 | Schulte et al. | 128/786 |
| 5,300,106 | 4/1994 | Dah et al. | 607/119 |
| 5,314,462 | 5/1994 | Heil et al. | 607/128 |
| 5,314,464 | 5/1994 | KenKnight et al. | 607/132 |
| 5,342,407 | 8/1994 | Dahl et al. | 607/129 |

(List continued on next page.)

FOREIGN PATENT DOCUMENTS

| | | |
|---|---|---|
| 0709111 | 5/1996 | European Pat. Off. . |
| 0813886 | 12/1997 | European Pat. Off. . |
| 2949782 | 6/1981 | Germany . |
| WO95/08365 | 3/1995 | WIPO . |

*Primary Examiner*—Scott M. Getzow
*Attorney, Agent, or Firm*—Schwegman, Lundberg, Woessner & Kluth P.A.

[57] ABSTRACT

A method and system for discriminating atrial and ventricular signal components from a single heart lead, and for using this information for identifying an arrhythmia condition as being atrial or ventricular in origin. The invention is effective in identifying P waves occurring in complex signal which includes relatively stronger R waves or other ventricular artifacts which mask the P waves. The contribution of the R wave signal to the complex signal is obtained by filtering, time windowing and transfer function estimation, then the R wave estimate is subtracted from the combined signal to leave the P wave. The ratio of P waves to R waves, P—P and R—R intervals, and their ratios to one another and to fixed values can be estimated, and used in a comparison to discriminate between atrial and ventricular arrhythmia, to thereby enable appropriate treatment.

8 Claims, 9 Drawing Sheets

U.S. PATENT DOCUMENTS

| | | | |
|---|---|---|---|
| 5,360,442 | 11/1994 | Dahl et al. | 607/129 |
| 5,370,663 | 12/1994 | Lin | 607/5 |
| 5,391,200 | 2/1995 | KenKnight et al. | 607/129 |
| 5,397,342 | 3/1995 | Heil, Jr. et al. | 607/129 |
| 5,411,527 | 5/1995 | Alt | 607/5 |
| 5,425,756 | 6/1995 | Heil, Jr. et al. | 607/128 |
| 5,443,485 | 8/1995 | Housworth et al. | 607/28 |
| 5,456,706 | 10/1995 | Pless et al. | 607/122 |
| 5,496,362 | 3/1996 | KenKnight et al. | 607/129 |
| 5,500,008 | 3/1996 | Fain | 607/5 |
| 5,514,174 | 5/1996 | Heil, Jr. et al. | 607/128 |
| 5,527,344 | 6/1996 | Arzbaecher et al. | 607/3 |
| 5,545,202 | 8/1996 | Dahl et al. | 607/129 |
| 5,545,205 | 8/1996 | Schulte et al. | 607/123 |
| 5,571,162 | 11/1996 | Lin | 607/122 |
| 5,603,732 | 2/1997 | Dahl et al. | 607/129 |
| 5,620,451 | 4/1997 | Rosborough | 606/108 |
| 5,628,778 | 5/1997 | Kruse et al. | 607/125 |
| 5,643,328 | 7/1997 | Cooke et al. | 607/36 |
| 5,654,030 | 8/1997 | Munshi et al. | 427/2.24 |
| 5,674,274 | 10/1997 | Morgan et al. | 607/123 |
| 5,683,443 | 11/1997 | Munshi et al. | 607/121 |
| 5,772,693 | 6/1998 | Brownlee | 607/123 |
| 5,776,072 | 7/1998 | Hsu et al. | 600/518 |
| 5,782,884 | 7/1998 | Stotts et al. | 607/17 |
| 5,782,898 | 7/1998 | Dahln et al. | 607/119 |
| 5,814,088 | 9/1998 | Paul et al. | 607/28 |
| 5,843,153 | 12/1998 | Johnston et al. | 607/122 |
| 5,851,227 | 12/1998 | Spehr | 607/126 |
| 5,871,532 | 2/1999 | Schroeppel | 607/128 |
| 5,876,431 | 3/1999 | Spehr et al. | 607/126 |
| 5,885,221 | 3/1999 | Hsu et al. | 600/515 |
| 5,916,243 | 6/1999 | KenKnight et al. | 607/129 |

FIG. 6A SIGNAL INPUT

FIG. 6B P-WAVE OUTPUT (LMS)

FIG. 6C RATE CHANNEL

ATRIAL AND VENTRICULAR CARDIAC LEAD HAVING A MECHANICAL BIAS

CROSS REFERENCE TO RELATED APPLICATIONS

This application is a division of U.S. patent application Ser. No. 08/996,355, filed on Dec. 22, 1997, now U.S. Pat. No. 5,885,221, which in turn is a continuation of U.S. patent application Ser. No. 08/579,872, filed Dec. 28, 1995, now U.S. Pat. No. 5,776,072, both of which are incorporated herein by reference.

FIELD OF THE INVENTION

This invention pertains to the field of detection and treatment of ventricular arrhythmias, and specifically to discriminating between arrhythmias of atrial origin and those which are of ventricular origin. In particular, the invention pertains to a method and system for discriminating atrial and ventricular signals from a signal received from a single lead, or a pair of leads, where the received signal contains cross-coupled atrial and ventricular information.

BACKGROUND OF THE PRIOR ART

The detection and treatment of ventricular arrhythmias by implantable devices is a proven technique for patients with serious heart conditions. Such devices contain an energy source, an electrode lead system in contact in the heart, a sensing system to detect the onset and type of arrhythmia, and a pulse generator for delivering pulses to treat the arrhythmia. Such devices may also include systems for detecting ventricular fibrillation, and for delivering defibrillation shocks.

One technique for detecting arrhythmias involves comparing the number of atrial P waves to the number of ventricular R waves occurring in an interval. This may be done by counting P waves and R waves as received by an endocardial lead system. If the two counts do not match, a determination of atrial or ventricular arrythmia can be made. However, if the P waves and R waves cannot be accurately discriminated from each other, the accuracy of the determination of arrythmia is impaired.

The reliable sensing of ventricular arrhythmia is critical, and is sometimes difficult because in many lead and sensing systems ventricular signals are combined or cross-coupled with atrial signals. Discrimination is further complicated by the fact that atrial and ventricular components will occur at different rates in the case of arrhythmias. This is a problem in devices which have only one lead in the ventricle, because discriminating atrial from ventricular arrhythmia is very difficult, and it is important to treat the patient appropriately. Examples of atrial arrhythmia include exercise (ST) or AF, AFL, SVT. Atrial arrhythmia is better left untreated by the ventricular defibrillator, but ventricular arrhythmia may be fatal and accordingly must be treated immediately.

Prior art techniques have generally relied on two strategies. One is to use two separate leads for the atrium and ventricle, with sensing electrodes positioned to maximize receiving the desired signals with minimum cross-coupling or unwanted contribution from the other. This technique can be successful, but requiring two separate leads is a disadvantage.

The other prior art technique is to use a single lead in the ventricle and to try to use electronic filtering to separate the atrial and ventricular signals received on this single lead. This has not been entirely successful in the prior art because the nature of the two signals, in terms of frequency and rate, makes them difficult to distinguish. In particular, tracking relatively small atrial P waves in the presence of larger far-field ventricular effects is very difficult in arrhythmia. Because of this, current devices with one ventricular lead cannot always discriminate atrial from ventricular signals, resulting in "inappropriate shocks".

SUMMARY OF THE INVENTION

To overcome these problems, the present invention provides a system and method using one ventricular lead, which discriminates between atrial and ventricular signals with greater accuracy than prior single lead devices. As explained in detail below, we have provided an improved method and system for discriminating between atrial and ventricular events through special signal analysis and filtering techniques provided by this invention. The invention is sufficiently accurate at discrimination that a single endocardial lead may be used, although the invention may also be used with multi-lead systems.

Improved discrimination of atrial and ventricular events permits improved effectiveness in the separate detection of atrial or ventricular arrhythmias, so that appropriate treatment decisions may be made immediately.

According to another aspect of the invention, an improved defibrillator system includes an single endocardial lead system for placement in electrical contact with the atrium and ventricle of the heart and a sensing system attached to lead for monitoring electrical activity. The sensing system detects the occurrence of and discriminates between R waves and P waves, even when the P waves are much weaker and obscured by the stronger ventricular signals. In a preferred form, the invention may be used with a single lead system having an atrial enhancement ring and special shape to improve the P to R signal ratio of the detected P waves.

According to another feature of the invention, instead of trying to directly extract filtered P waves from the combined channel signal, the system of the present invention uses the approach of accurately estimating the contribution of R waves to the combined channel, then subtracting these contributions from the combined channel, to leave only the P waves. From this residue, the ratio of P waves to R waves may then be estimated or measured to identify an arrhythmia as being of atrial or ventricular origin.

These and other features and advantages of the invention will become apparent from the following description of the preferred embodiments of the invention.

DESCRIPTION OF THE PREFERRED EMBODIMENT

The preferred embodiment of the invention is illustrated herein as included in an implantable heart defibrillator/pacemaker, which may include numerous pacing modes as is generally known in the art. The system and method of the invention could also be implemented in an external defibrillator/monitor.

Figure 1:
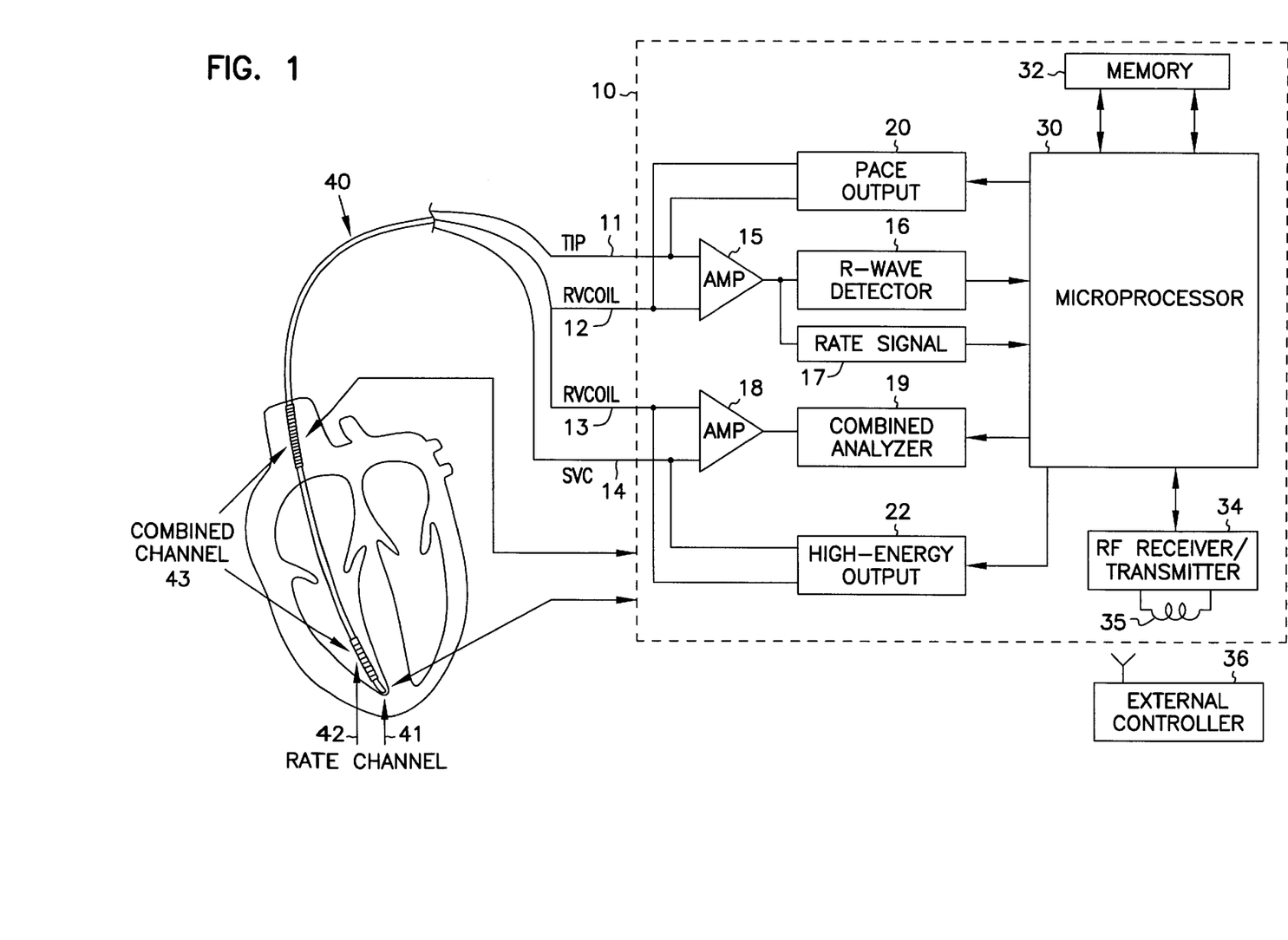
FIG. 1 is a block diagram of an implantable defibrillator/pacemaker of the type with which the present invention may be implemented, including a diagrammatic representation of an endocardial lead system placed in a heart.

In FIG. 1, defibrillator/pacemaker 10 is shown in block diagram form. It includes terminals, labelled with reference numbers 11, 12, 13, and 14, for connection to a lead system 40. Lead system 40 is preferably an endocardial lead, although other types could also be used within the scope of the invention. An endocardial lead is adapted for placement in the right ventricle. The lead system includes a number of electrodes or electrical contacts. The tip electrode 41 is at the distal end of the lead system, and connects electrically through a conductor provided in the lead, for connection to terminal 11. Lead system 40 also includes an RV coil electrode 42 spaced near the distal end for placement in the right ventricle, and this RV coil electrode connects through an internal conductor in the lead and is connected both to terminals 12 and 13. The lead system 40 also includes an SVC coil electrode 43, positioned a distance back from the distal end of the electrode for placement in the superior vena cava as indicated. The SVC electrode is connected to terminal 14.

In the standard terminology used in this specification, the heart signal developed at the tip 41 with reference to RV coil 42 is referred to as the R channel or signal, as it is normally largely the ventricular depolarization signal. Alternatively, the signal from tip 41 to the device 10 housing, or 'can' as it is also called, can also be used for this. The signal at RV coil 42 with reference to SVC electrode 43 is referred to as the combined channel or signal. This signal necessarily is a combination of effects from the ventricle and the atrium, and is the signal used in the present invention to discriminate the atrial and ventricular signals. Alternatively, the signal from SVC coil 43 to the device 10 housing can also be used for this.

Figure 7A:
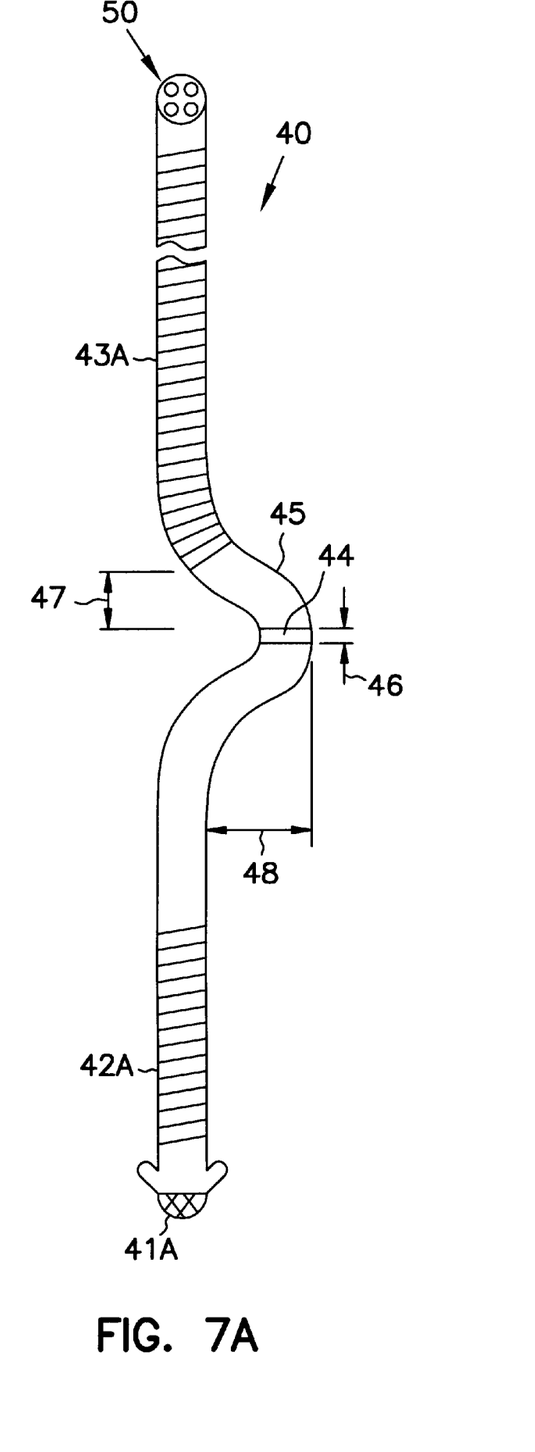
FIGS. 7A and 7B are a view of an alternative form of a lead system which gives improved performance with the system and method of the present invention.
Figure 7B:
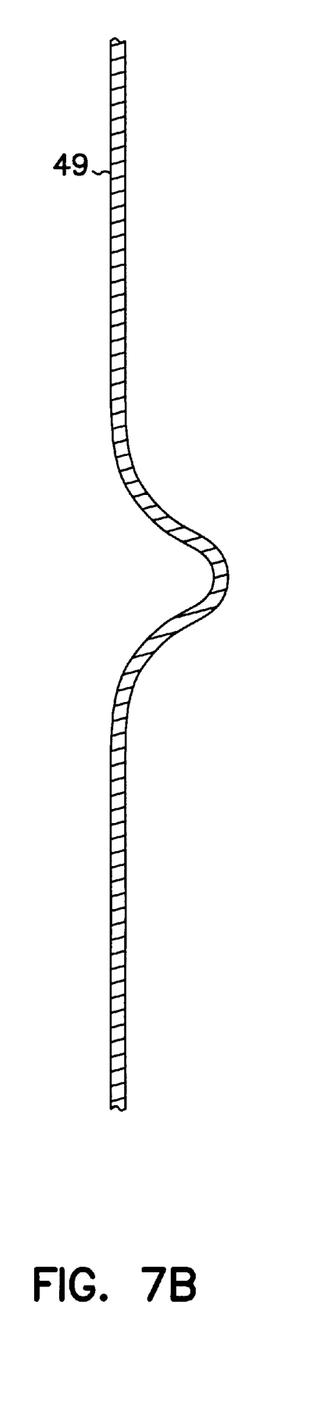

FIGS. 7A and 7B show an alternative form of a lead which gives improved performance with the system and method of the present invention. As described above, the system of FIG. 1 shows a conventional endocardial lead, having standard electrodes for the RV tip, RV coil, and SVC coil on a generally flexible multi-lumen tubular body. The modified lead of FIG. 7A has the same components, plus an additional SVC sense ring, and a curved shape to hold it into contact with the interior wall of the atrium or superior vena cava. Specifically, lead 40A of FIG. 7A has an RV tip electrode 41A, an RV coil 42A, an SVC coil 43A, which may be similar in configuration and operation to their corresponding parts in lead system 40. In addition, lead 40A has an atrial sense ring 44A as indicated in FIG. 7. Lead 40a has a double-bend portion comprising a semi-flexible, semi-rigid arch which is set in the lead to form a lateral protrusion 45 to mechanically bias atrial sense ring 44A into contact with the inside wall of the atrium. Protrusion 45 is spaced from the tip of the lead so as to be placed in the atrium when the lead is in its use position with the RV tip is in the ventricle. Atrial sense ring 44a is a small ring electrode placed around the lead at the lateral protrusion 45, in a position where it will be in contact with the atrium when the lead is placed in the heart as indicated in FIG. 1. The advantage of this configuration is that the atrial sense ring is held in direct contact with the atrial wall, which provides better signals for P wave discrimination, as compared with lead designs which do not ensure such direct contact. This is especially important in arrythmia situations, where the signal amplitude in the atrium may be small and not well defined.

The preferred lead of FIG. 7A may be constructed generally according to known techniques for multi-lumen intravascular electrode leads, an example of which is shown and described in U.S. Pat. No. 4,603,705 to Speicher et al. The addition of atrial sense ring 44A will require an additional conductor inside the body of lead 40A. For this reason, lead 40A of FIG. 7A has four lumens, which are seen in the section 50 drawn at the top of the FIG. 7A. The four lumens are the atrial ring lumen, the distal RV coil lumen, the proximal SVC coil lumen, and the lumen for the stylet coil which may also serve as the conductor for the tip electrode. A stylette coil is normally found in multi-lumen intravascular electrode leads, consisting of a flexible metallic coil in one of the lumens serving to receive a stylette as is generally known for facilitating directional control of the lead during its placement in the heart. Lead 40A likewise has a stylette coil in one of the lumens which are seen in section 50, and this stylette coil is indicated by reference number 49 in FIG. 7B. The double-bend portion of stylette coil 49 which forms lateral protrusion 45 may preferably be formed by forming the bends in the stylette coil to take a 'set' in which the protrusion 45 is shaped as shown in FIG. 7A. The stylette coil has sufficient flexibility to straighten for the stylette, then return towards the set shape after removal of the stylette.

In the presently preferred embodiment, the distance 48 of the offset of protrusion 45 as indicated in FIG. 7A is from 1 to 3 centimeters. The length or axial extent 46 of atrial sense ring 44A as indicated in FIG. 7A is 0.5 to 3.0 millimeters. The axial distance of atrial sense ring 44A from the SVC coil 43A as indicated in FIG. 7A is 0.5 to 3.0 centimeters.

Figure 3:
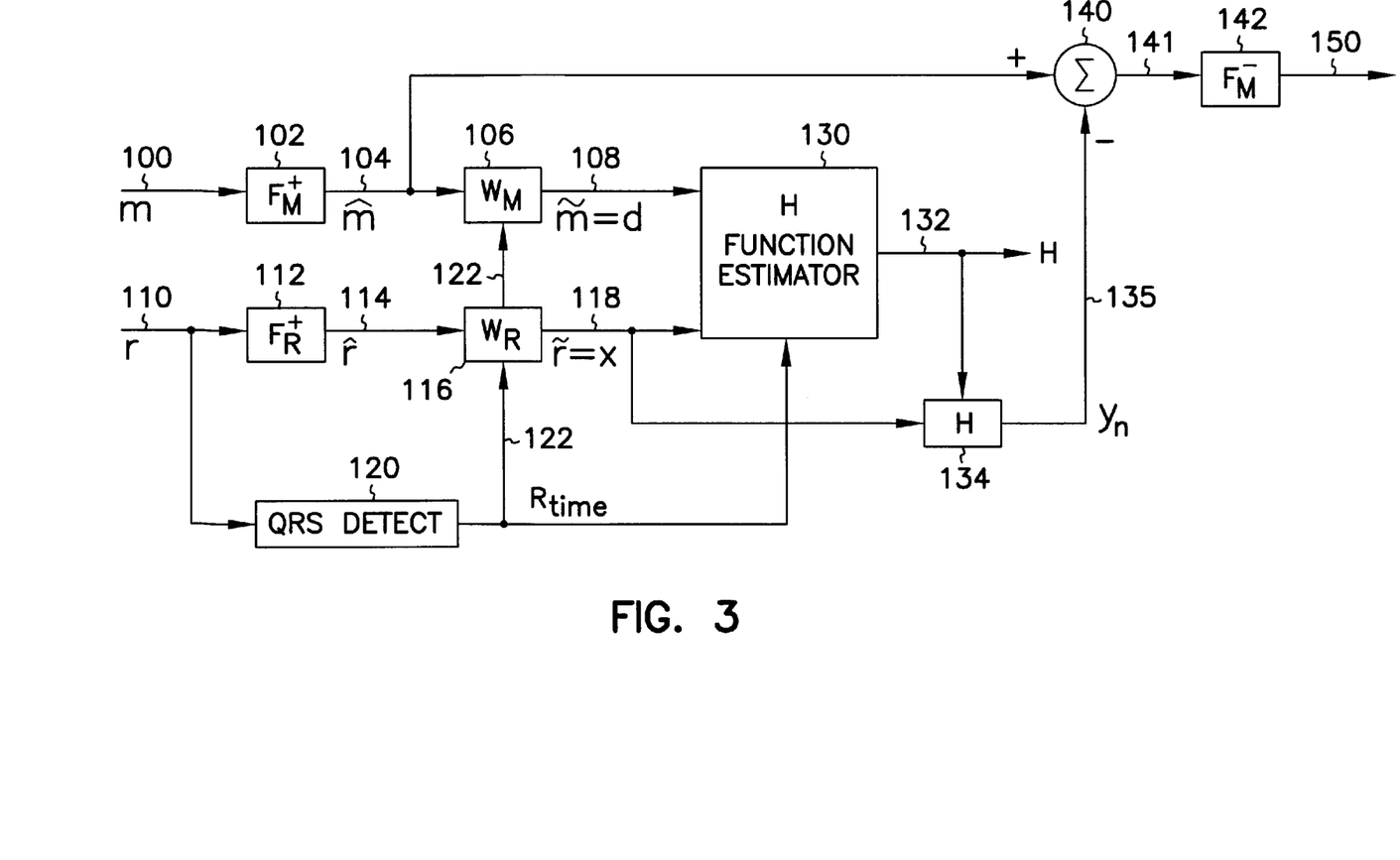
FIG. 3 is block/flow diagram of the operation of the P wave extraction method of the invention.
Figure 5:
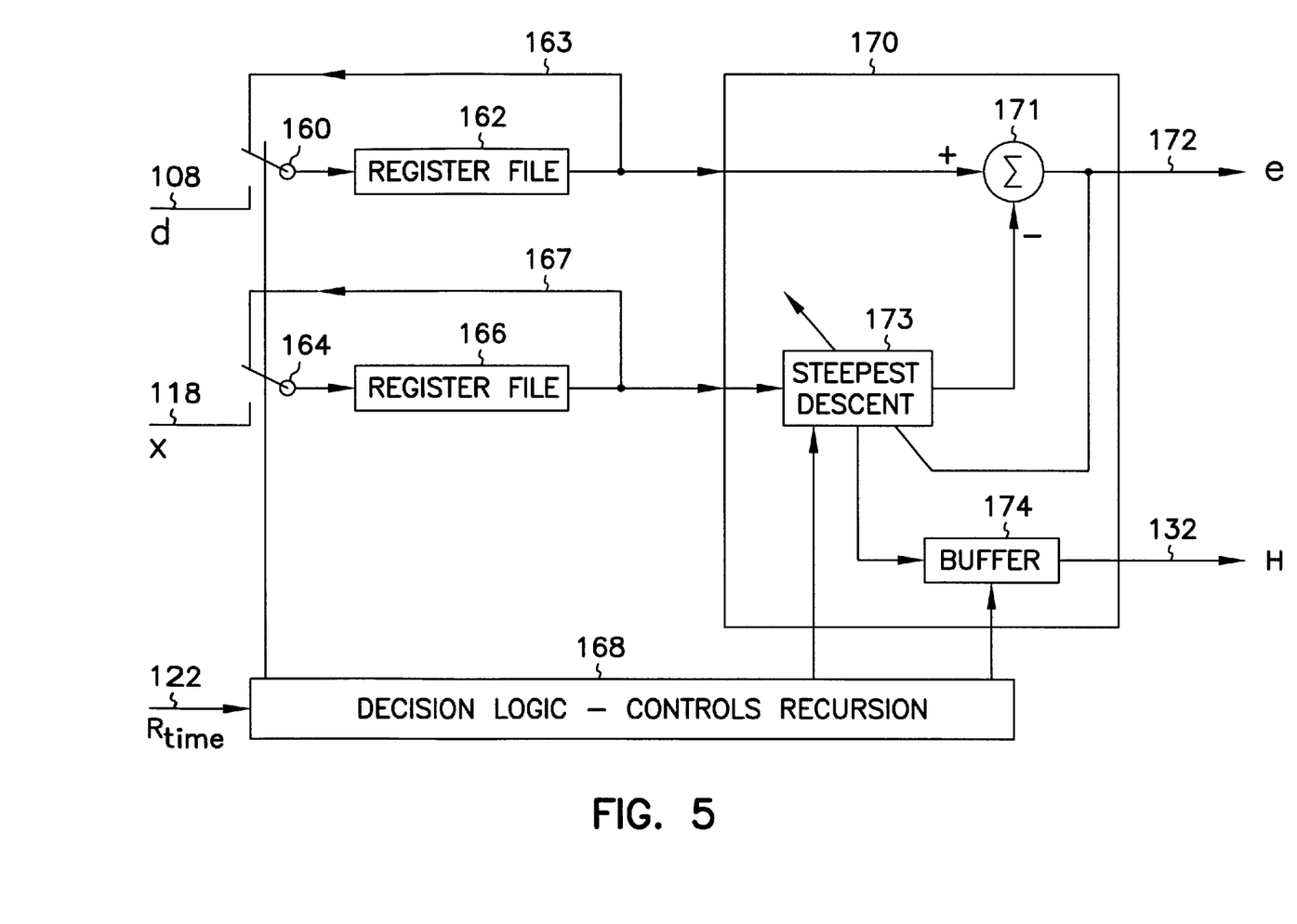
FIG. 5 is a block/flow diagram of the H function estimator block of FIG. 3.

The connection to atrial sense ring 44A is brought out and connected as one of the inputs to amplifier 18, in place of the SVC lead 14 as shown in FIG. 1. In this manner, the atrial signals sensed at atrial sense ring 44A are used, together with the signals from RV coil 42A, as the combined channel. Alternatively, the signal from atrial sense ring 44A can be referenced to the device housing 10. Other than as described above, the configuration and operation of FIG. 1, and the signal processing described below with reference to FIGS. 3 and 5, is the same for either lead system. The advantage to using the modified lead of FIGS. 7A and 7B is that it provides a better signal-to-noise ratio for the atrial signals, specifically a better P to R ratio, and facilitates the recovery of the P waves by the filtering system of the invention.

The defibrillator/pacemaker 10 is a programmable microprocessor-based system, with a microprocessor indicated by reference number 30. Microprocessor 30 operates in conjunction with a memory 32, which contains parameters for various pacing and sensing modes. Microprocessor 30 includes means for communicating with an internal controller, in the form of an RF receiver/transmitter 34. This includes a wire loop antenna 35, whereby it may receive and transmit signals to and from an external controller 36. In this manner, programming inputs can be applied to the microprocessor of the defibrillator/pacemaker after implant, and stored data on the operation of the system in response to patient needs can be read out for medical and analysis.

In the defibrillator/pacemaker of FIG. 1, the tip 41 and RV coil 42, connected through leads 11 and 12, are applied to a sense amplifier 15, whose output is shown connected to an R wave detector 16 and a rate signal circuit 17. These components serve to amplify and sense the QRS wave of the heart, and the R channel signal, and apply signals indicative thereof to a microprocessor 30. Among other things, microprocessor 30 responds to the R wave detector 16, and provides pacing signals to a pace output circuit 20, as needed according to the programmed pacing mode. Output circuit 20 provides output pacing signals to terminals 11 and 12, which connect as previously indicated to the tip and RV coil electrodes, for normal pacing.

The RV coil 42 and SVC coil 43 (or SVC ring 44a, in the embodiment of FIG. 7) are connected through leads 11 and 12, and are applied to a sense amplifier 18, whose output is shown connected to combined channel analyzer 19. These components serve to amplify and sense the combined signal of the heart and apply signals indicative thereof to microprocessor 30.

The defibrillation portion of the defibrillator/pacemaker FIG. 1 includes a high energy output pulse generator 22, which operates under the control of microprocessor 30, as indicated. Pulse generator 22 is connected to terminals 13 and 14, which connect to the RV coil and SVC as previously mentioned. In this manner, defibrillation shocks can be provided through the endocardial lead system 40 for defibrillation when called for by the microprocessor, and specifically the software implementation of control algorithms.

Figure 2A:
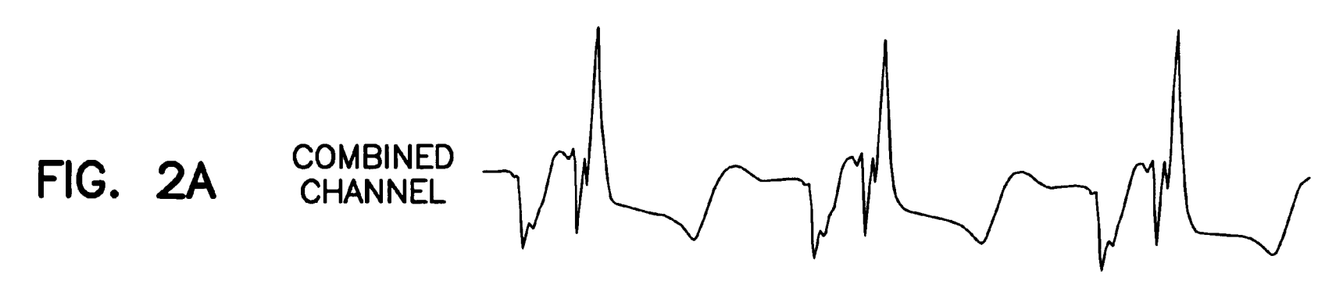
FIGS. 2A, 2B and 2C are a set of three related waveforms illustrating the operation of the present invention: a combined channel, the corresponding Rate channel signal, and the extracted P wave developed therefrom by the operation of the present invention.
Figure 2B:
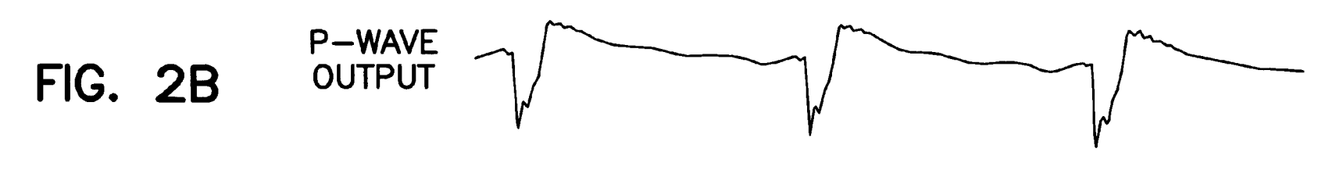
Figure 2C:
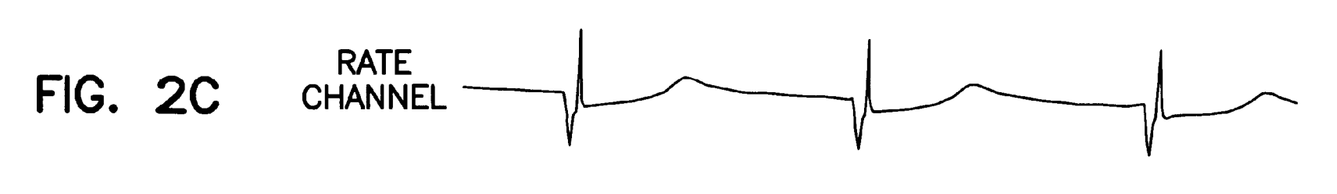

FIG. 2 shows a waveform, labelled "Combined Channel", representative of the combined signal of an endocardial lead, such as might be obtained in analyzer 19 of FIG. 1. The FIG. 2 waveform labelled "Rate Channel" is representative of the rate signal of an endocardial lead such as might be obtained at block 17 of FIG. 1. FIG. 2 is an example of normal rhythm, in which the P waves and QRS match. The waveform labelled "P-Wave Output" is the isolated P Wave recovered from the combined channel by the operation of the invention, as described below.

The successful treatment of ventricular arrhythmias depends upon reliable detection thereof. To detect arrhythmias, it is necessary to separately measure the P waves and R waves, so that they can be compared to determine if arrhythmia exists, and whether it is atrial or ventricular. The combined signal inherently includes contributions from the atrium and ventricle, as is apparent from FIG. 2, and from a consideration of the location of sensing of the combined signal. Separation of the two by normal filtering techniques is difficult. Note that the regular timing relationship between the P wave and R wave seen in FIG. 2 cannot in general be used as a basis for separating the signals, because in the case of arrhythmia, this timing is disturbed.

Instead of trying to directly extract filtered P waves from the combined signal, the system of the present invention uses the approach of extracting filtered R waves, which are obtained to a high degree of accuracy by an estimation algorithm, then subtracting them from the original combined signal, to leave only the P waves.

FIG. 3 shows the main operation of the system and method of the present invention, starting from the combined signal, m, and rate signal, r, from the device of FIG. 1. In this Figure, and in FIG. 5, the various steps are represented as blocks or functions and paths, and it will be appreciated by those skilled in the art that the various functions could be implemented by digital circuits, or by software modules operating in microprocessor 30, which is the preferred method.

The Path 100 conveys the signal m to a digital filter 102. The output of this function on path 104 is applied to a windowing function 106, and also to a summer function 140. Path 110 conveys the signal r to a filter function 112. The output of this function on path 114 is applied to a windowing function 116 to leave only signal components that are to be canceled. The signal r is also applied to a QRS detect function 120, the output of which is applied by path 122 to window functions 106 and 116, and H Transfer Estimate block 130. QRS detect 120 supplies a timing signal on the R wave occurrence.

The filters 102 and 112 are referred to as $F_M^+$ and $F_R^+$, respectively. They are fixed FIR Z-domain transfer filters which are identical except for delay; $F_M^+$ having a slightly greater delay. The filter $FM_M^+ = (1-aZ^{-1})Z^{-m}$. These filters are used to enhance the QRS-related depolarization event in both the m and r signals, while reducing the T-wave and P wave contributions thereto.

Figure 4A:
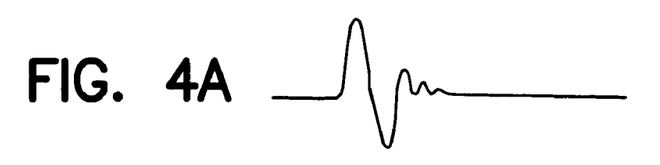
FIGS. 4A, 4B, 4C and 4D are related waveforms illustrating the operation of portions of FIG. 3.
Figure 4B:
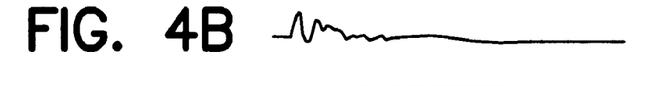
Figures 4C, 4D:
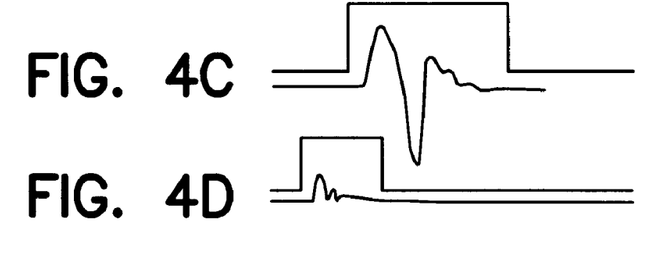

The two window functions 106,116, labelled $W_M$ and $W_R$ are time windows which operate on the filtered outputs $\tilde{m}$ and $\tilde{r}$ to define time windows of interest for the operation of the estimator 130. This is shown in FIGS. 4A and 4B. There is greater delay in the signal $\tilde{m}$, and its window function, than for $\tilde{r}$ and its window function. The delays are useful for best results so that the function H will have some impulse response of R components prior to the rate channel. The difference in delays for $W_M$ and $W_R$ is important for the estimation of the function H in block 130, because H is non-causal, and therefore some response is needed prior the signal. The amount of difference in delay is empirically determined for a given lead and circuit design, to give the best P wave extraction. These windows effectively localize the attention of the transfer function estimator 130 to the time of the QRS related depolarization event. Their outputs $\tilde{m}$ and $\tilde{r}$ are shown in FIGS. 4C and 4D. The four blocks 102, 112, 106, 116 are thus used to carve out a time-frequency window having characteristics matched to minimize ventricular artifacts in the final P wave.

The function 130 provides an estimate of the transfer function H which maps $\tilde{r}$ to $\tilde{m}$. The preferred implementation of function 130 is a least mean square (LMS) learning algorithm, and is described in detail below. Once the transfer function $H_n$ has been obtained for an $\tilde{r}$, $\tilde{m}$ pair, it is available at path 132 for use in function 134.

Function 134 uses $H_n$ and $\tilde{r}_n$ to produce the convolution thereof, $Y_n$. It is important to note that, because of the relationship of H, $\tilde{m}$ and $\tilde{r}$, $Y_n$ is a measure of the contribution of the ventricular components, i.e. the R wave, to the total combined signal. This estimate of the QRS may then be subtracted from the combined signal, leaving only the atrial P wave. Summer 140 is used for this function.

The final step of FIG. 3 uses filter 142 to recover the P wave output signal of FIG. 2. Filter 142, $F_M^-$ is the inverse in time domain of filter 102, $F_M^+$. Specifically, $$F_M^- = \frac{1}{F_M(Z)}.$$

The transfer function H estimator 130 is shown in greater detail in FIG. 5. The signal m̃=d is applied to a switching function 160, which is represented symbolically as a physical switch, but which can also be implemented as a software function. Switch 160 connects to the input of a register file 162. The output of this file connects via path 163 back to another input to switch 160, and also to summer 171 of LMS estimator 170. Similarly, The signal r̃=x is applied to another switching function 164, which connects to the input of a register file 166. The output of this file connects via path 167 back to another input to switch 164 and also to the Steepest Descent function 173 of LMS estimator 170. The $R_{time}$ signal from path 122 connects to decision logic 168, which controls the recursion of LMS estimator 170.

In operation, for each occurrence n, as signified by the $R_{time}$ signal, switches 160 and 164 fill their respective register files 162, 166 with vectors of their applied data, then close, so that the data vectors are clocked through and recirculate through the register files. On each pass, LMS estimator 170 tries to develop a vector H, in buffer 174, with increasing precision. Element 173 updates H based on error. After sufficient recursions, as determined either by count or examination of residual error, the estimate of H is complete, and is used in the function of FIG. 3 as previously described.

In the above description of FIG. 3, the filters and windows chosen are only by way of example, as other types could be used. The filters chosen should be realizable and stable, and have realizable, stable inverses. Alternatively, it may not be necessary to provide or use the inverse filter 142, in which case the signal at 141 can be used as the output.

Figure 6A:
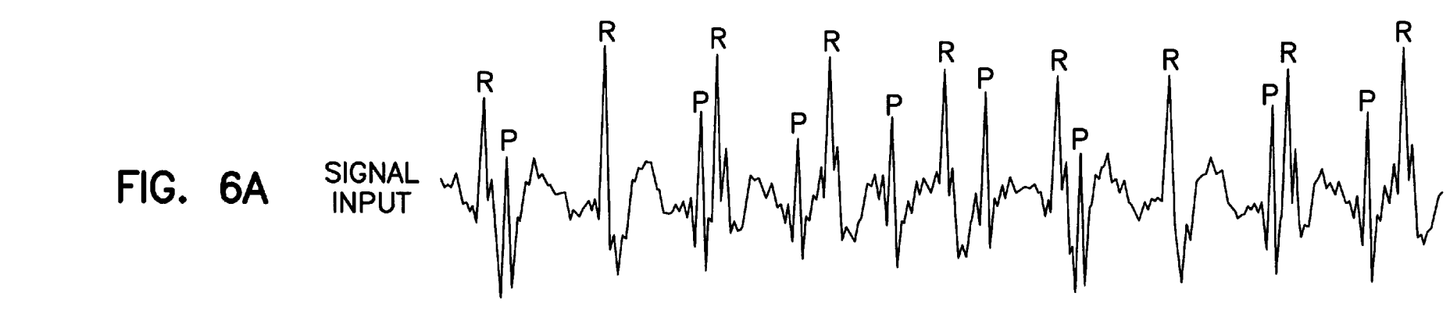
FIGS. 6A, 6B, and 6C are a set of three related waveforms similar to FIGS. 2A, 2B, 2C illustrating the operation of the present invention on a set of signals in atrial arrythmia.
Figure 6B:
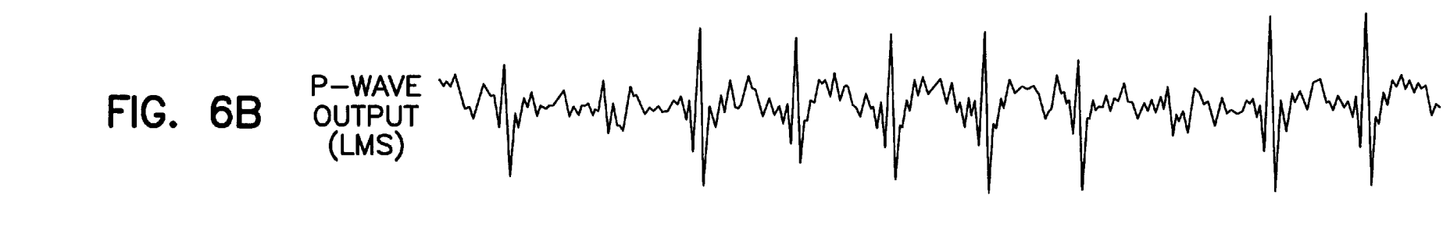
Figure 6C:
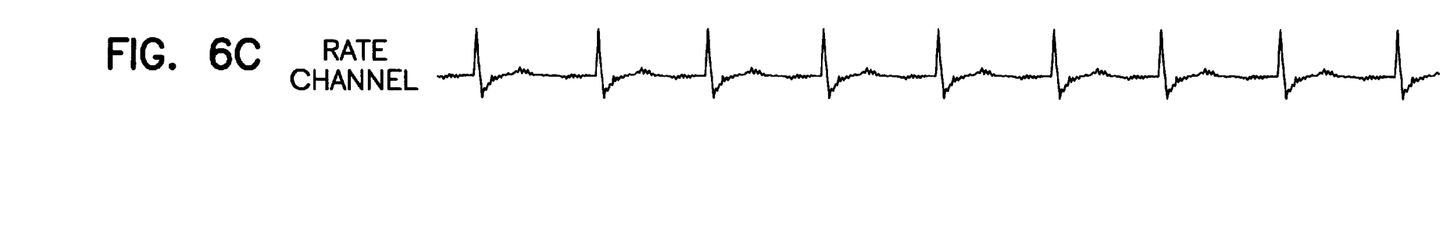

The above discussion of FIGS. 2 and 3 was based on normal heart rhythm waveforms for purposes of simplicity. In the case of arrhythmia, the ventricular and atrial rates will differ, and the combined waveform becomes more complex, as seen in FIG. 6. However, the method and system of the invention continues to operate to separate the P wave from ventricular artifacts, except for the case when the P wave occurs at the same time (within the time window) of the R wave. However, all other instances will be recovered, and will provide sufficient accurate data to make a determination of atrial and ventricular activity. This operation is illustrated in FIG. 6, wherein the top trace, labelled "Signal Input" is the combined channel, containing both atrial and ventricular information. Peaks due to R waves and P waves are indicated with an R or P, respectively. Note that there is not a fixed timing relationship between the two, in this example. The rate channel signal is easily extracted from the combined signal, and is shown in the third trace in FIG. 6. The second trace, labelled P-Wave Output, is the result of application of the method of FIG. 3 on the input signal of the first trace of FIG. 6. The P wave contribution to the combined signal has been effectively removed.

According to another feature of the invention, the separation of P waves may be used for making a determination of atrial or ventricular arrhythmia. This once the P waves have been separated from the combined signal, they can be counted over a period of time. The R waves may also be counted over the same time using the R channel. It may only be necessary to start such counting if the sensed ventricular rate if above the tachy threshold, e.g. 180 beats per minute or so.

Figure 8:
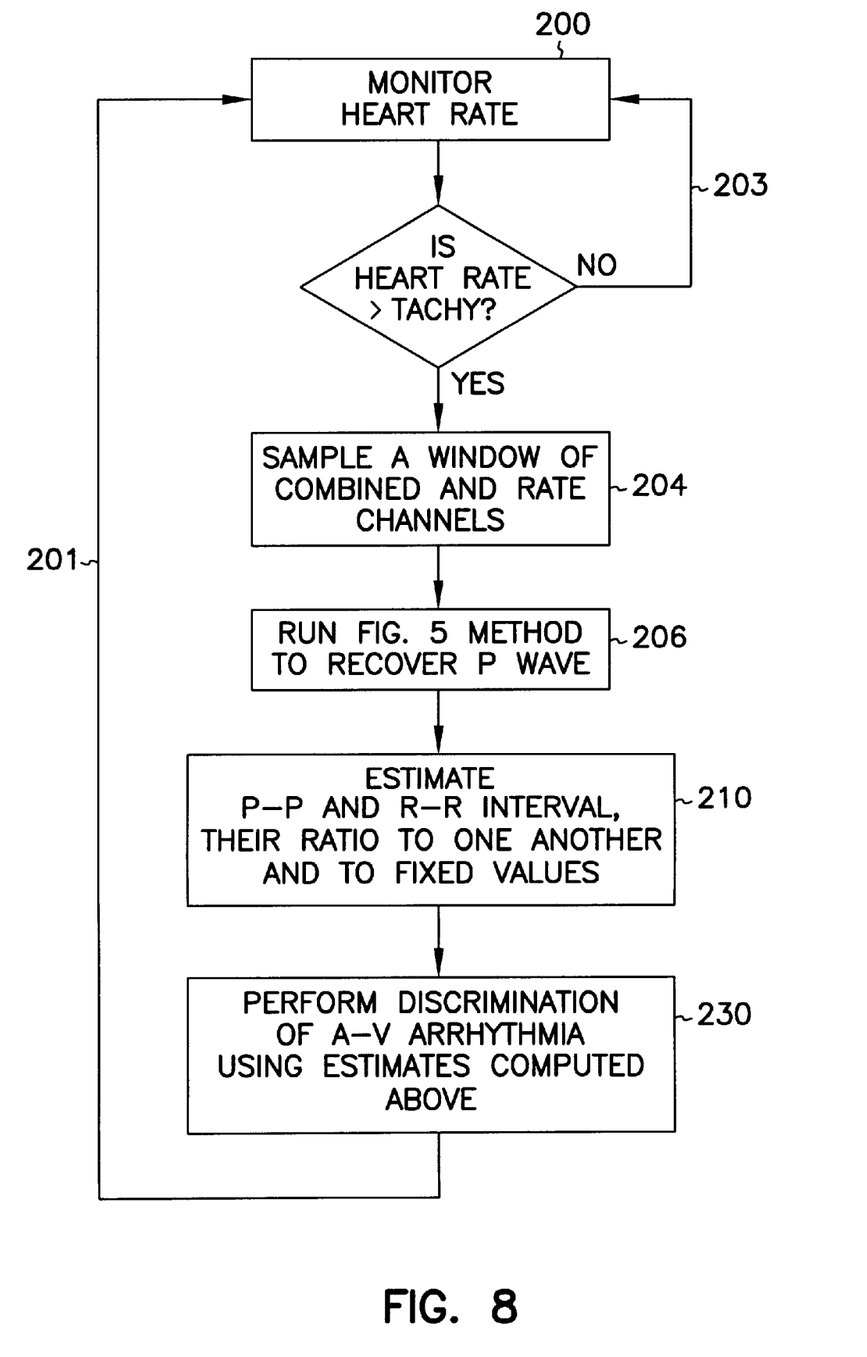
FIG. 8 is a flow diagram illustrating the overall operation of a heart monitoring system incorporating the present invention.

The overall operation of a heart monitoring system incorporating the present invention is shown in greater detail in FIG. 8. At step 200, the system monitors the basic heart rate of the heart through the R channel 17. At step 202, which may be a software step programmed into microprocessor 30, this rate is compared to a preset or preprogramable tachycardia rate. If the rate is not greater than, or is less than the tachycardia rate, control branches back on path 203 to step 200, which is continually repeated during the monitoring process.

If, however, the monitored heart rate as tested at step 202 is above the tachycardia limit, control branches to step 204. Step 204 samples a window of the combined and R channels, in the manner as previously described with respect to FIGS. 3 and 4, A–D, and at step 206, the filtering process previously described with respect to FIGS. 3 and 5 is run to minimize the R wave in the combined signal, and to thereby extract P wave signals.

Control then passes to step 210, which estimates the P to R ratio, the P—P interval, the R—R interval, and the P—P interval and R—R interval to fixed thresholds, where P is the number of P waves from the processed combined signal, and R is the number of R waves, occurring over a given sample interval. These estimation steps may be done by counting, or other known techniques. At step 230, these estimates are analyzed and compared in order to determine or classify the nature of the tachycardia condition. This is explained in greater detail with reference to FIG. 9. Control then branches back on path 201 to step 200, to continually repeat and update the process just described.

Figure 9:
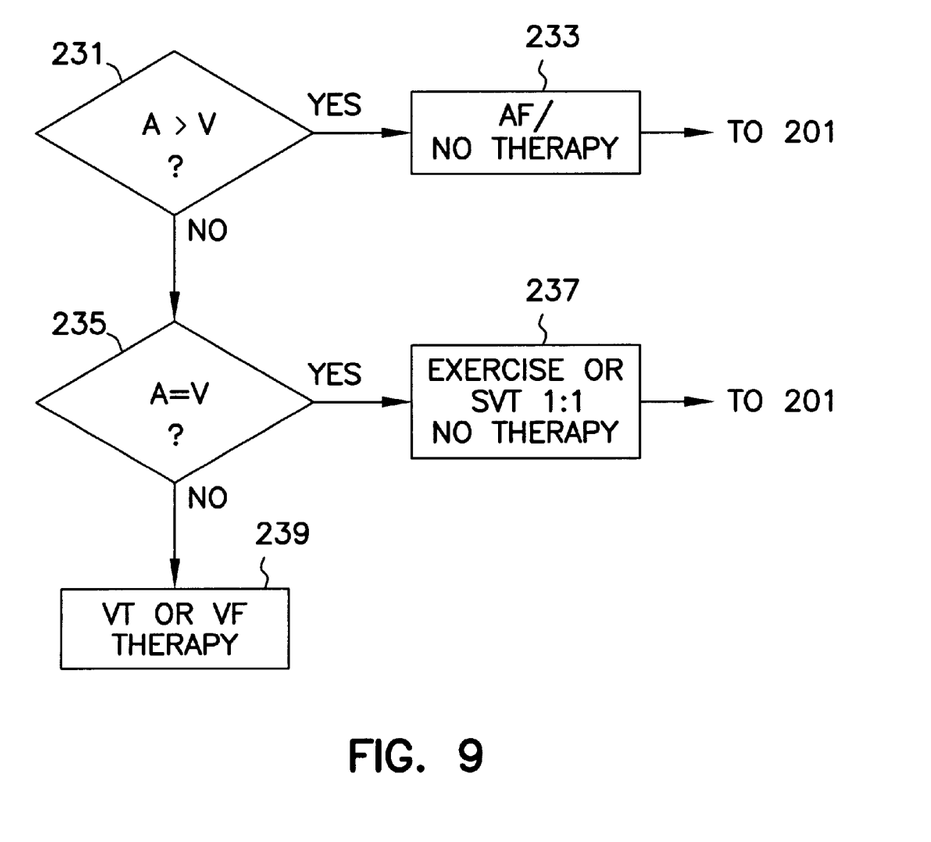
FIG. 9 is a flow diagram illustrating the A-V discrimination step of FIG. 8 in greater detail.

The discrimination or classification of tachycardia conditions, which is step 230 of FIG. 8, is shown in greater detail in FIG. 9. In FIG. 9, step 231 tests whether the count or estimate of atrial events is greater than the count or estimate of ventricular events, i.e., whether the number of P waves is greater than the number of R waves over the sample. If the answer is "yes," control branches to step 233, which declares or determines that the tachycardia is AF (atrial fibrillation), and no therapy is needed. Control then branches back on path 201 to start the process again.

If, however, at step 231, the atrial count or estimate is not greater than ventricular, control passes to step 235. If the atrial count or estimate equals the ventricular estimate or count (within a predetermined small plus or minus count variation to accommodate sampling errors), control branches to block 237, at which point the determination is made that the tachycardia is due to exercise or SVT with a one-to-one ratio, in which case no therapy is indicated. Control branches back on lead 201 to resume the monitoring process.

If, at step 235, the atrial count or estimate does not equal the ventricular estimate or count (within the sampling error allowance), control passes to block 239. To reach this path, the ventricular count will have to be greater than the atrial count. At block 239, a determination is made or declared that the tachycardia is due to ventricular tachycardia (VT) or ventricular fibrillation (VF), either of which calls for an indication of appropriate therapy to be applied by the device, as is generally known in the art.

It will be seen from the foregoing description that the present invention provides an improved method and system for discriminating atrial and ventricular signal components from a single heart lead, and for using this information for identifying an arrhythmia condition as being atrial or ventricular in origin, to thereby enable appropriate treatment.

We claim:

1. An endocardial heart lead system, comprising:

an elongated generally flexible tubular housing having a proximal end for connection to a device and distal end for placement, in a use position, through the right atrium to the right ventricle of a heart;

a pair of ventricular electrodes respectively at and adjacent the distal end of the lead for contact in the ventricle and receiving ventricular signals of the heart;

an SVC electrode positioned on the tubular housing at a position spaced from the distal end for placement in the superior vena cava when the lead system is in the heart;

an atrial electrode positioned on the tubular housing at a position spaced from the distal end and from the SVC electrode for placement in the atrium when the lead system is in the heart;

the tubular housing including conductors therein connected to the electrodes and for connection to a device at the proximal end; and the tubular housing having a curved portion, taking the form of a lateral protrusion along said tubular housing, in region of the atrial electrode to mechanically bias the atrial electrode into contact with the wall of the atrium of the heart when the lead system is in the use position.

2. The endocardial heart lead system according to claim 1, wherein the curved portion comprises a flexible arch formed in the tubular housing in the region thereof for placement in the atrium when the heart lead is in the use position, and wherein the atrial electrode is placed on the curve of the arch for holding in contact with the atrial wall by the resilience of the curved portion.

3. The endocardial heart lead system according to claim 2, wherein the tubular housing includes a stylette coil, and wherein the flexible arch is formed by bends in the stylette coil.

4. An endocardial heart lead system, comprising:

an elongate tubular housing having a proximal end for connection to a device and a distal end;

a pair of ventricular electrodes respectively at and adjacent the distal end of the lead;

an SVC electrode positioned on the housing at a position spaced from the distal end;

an atrial electrode positioned on the housing at a position spaced from the distal end and from the SVC electrode;

the tubular housing including conductors therein connected to the electrodes and for connection to a device at the proximal end; and the tubular housing having a lateral protrusion in region of the atrial electrode to position the atrial electrode into contact with the wall of the atrium of the heart when the lead is in a use position.

5. The endocardial heart lead system as recited in claim 4, wherein the lateral protrusion comprises a semi-rigid arch.

6. The endocardial heart lead system as recited in claim 4, wherein the atrial electrode comprises a ring around the lead at the lateral protrusion.

7. The endocardial heart lead system as recited in claim 4, wherein the protrusion is offset from approximately 1 to 3 centimeters.

8. The endocardial heart lead system as recited in claim 4, wherein the axial distance of the atrial electrode from the SVC electrode is approximately 0.5 to 3 centimeters.

* * * * *